United States Patent [19]

Takehara et al.

[11] Patent Number: 4,500,693

[45] Date of Patent: Feb. 19, 1985

[54] WATER SOLUBLE COPOLYMER METHOD FOR MANUFACTURE THEREFORE AND USE THEREOF

[75] Inventors: Hidetoshi Takehara, Tatsuno; Shorbu Shioji; Yohichi Nakagawa, both of Himeji, all of Japan

[73] Assignee: Nippon Shokubai Kagaku Kogyo Co., Ltd., Osaka, Japan

[21] Appl. No.: 614,695

[22] Filed: May 25, 1984

Related U.S. Application Data

[63] Continuation of Ser. No. 395,883, Jul. 7, 1982, abandoned.

[30] Foreign Application Priority Data

Jul. 7, 1981 [JP] Japan ................... 56-105027
Jul. 8, 1981 [JP] Japan ................... 56-105635
Feb. 26, 1982 [JP] Japan ................... 57-28863
Mar. 9, 1982 [JP] Japan ................... 57-35854

[51] Int. Cl.³ .......................................... C08F 220/04
[52] U.S. Cl. ................... 526/240; 526/287; 526/317; 526/332; 526/333
[58] Field of Search ............ 526/317, 332, 333, 240, 526/257, 277, 278, 287, 286

[56] References Cited

U.S. PATENT DOCUMENTS 4,267,103 5/1981 Cohen .................... 526/317

FOREIGN PATENT DOCUMENTS 1103947 2/1968 United Kingdom .

Primary Examiner—Paul R. Michl
Assistant Examiner—Alex H. Walker
Attorney, Agent, or Firm—Omri M. Behr

[57] ABSTRACT

A water-soluble copolymer useful for scale inhibitor and pigment dispersant, comprising 50 to 99.5 mol % of repeating units represented by the general formula I:

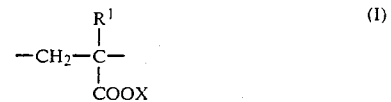

wherein, $R^1$ denotes a hydrogen atom or methyl group and X a hydrogen atom, alkali metal atom, alkaline earth metal atom, ammonium group, or organic amine group and 50 to 0.5 mol % of repeating units represented by the general formula II:

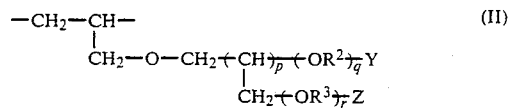

wherein, p denotes an integer of the value of 1 to 4, q and r independently denote 0 or an integer of the value of 0 to 100, $R^2$ and $R^3$ independently denote an alkylene group of 2 to 4 carbon atoms, and Y and Z independently denote a hydroxyl group, an alkoxy group of 1 to 4 carbon atoms, a monovalent phosphoric acid group or an alkali metal salt, alkaline earth metal salt, ammonium salt, or organic amine salt thereof or a mono- or di-ester thereof with an alkyl of 1 to 4 carbon atoms, a monovalent sulfonic acid group or an alkali metal salt, alkaline earth metal salt, ammonium salt, or organic amine salt thereof or an ester thereof with an alkyl of 1 to 4 carbon atoms.

22 Claims, 3 Drawing Figures

WATER SOLUBLE COPOLYMER METHOD FOR MANUFACTURE THEREFORE AND USE THEREOF

This application is a continuation of application Ser. No. 395,883, filed 7/7/82 now abandoned.

BACKGROUND OF THE INVENTION

1. Field of the Invention

This invention relates to a water-soluble copolymer, a method for the manufacture thereof, and use thereof. More particularly, this invention relates to a water-soluble copolymer composed of an acrylic acid-based component and an allyl ether-based component, a method for the manufacture thereof, and use thereof for scale-preventing agent and pigment dispersant.

2. Description of Prior Arts

As water-soluble polymers, the polymers such as polyacrylic acid, poly(ammonium acrylate), poly(sodium acrylate) and poly(sodium methacrylate) which are obtained by homopolymerizing or copolymerizing acrylic acid, methacrylic acid and alkali salts thereof have been known to the art. These water-soluble polymers are widely used as aqueous slurry dispersants for inorganic pigments and as scale-preventing agents in cooling water systems and wet dust collecting systems. As improved versions of these water-soluble polymers, there have been suggested copolymers of alkyl (meth)acrylates with acrylic acid and copolymers of hydroxyalkyl (meth)acrylates with acrylic acid. To date, however, there has been suggested not a single water-soluble polymer that possesses fully satisfactory properties.

An object of this invention, therefore, is to provide a novel water-soluble copolymer, a method for the manufacture thereof, and novel use thereof.

Another object of this invention is to provide a water-soluble copolymer which is useful as a scale-preventing agent and as a pigment dispersant.

SUMMARY OF THE INVENTION

The object described above are accomplished by a water-soluble copolymer, comprising 50 to 99.5 mol% of repeating units represented by the general formula I:

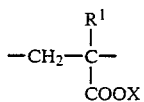

wherein, $R^1$ denotes a hydrogen atom or methyl group and X a hydrogen atom, alkali metal atom, alkaline earth metal atom, ammonium group or organic amine group, and 50 to 0.5 mol% of repeating units represented by the general formula II:

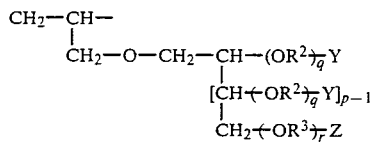

wherein, p denotes an integer of the value of 1 to 4, q and r independently denote O or an integer of the value of 1 to 100, $R^2$ and $R^3$ independently denote an alkylene group of 2 to 4 carbon atoms, and Y and Z independently denote a hydroxyl group, an alkoxy group of 1 to 4 carbon atoms, a monovalent phosphoric acid group or an alkali metal salt, alkaline earth metal salt, ammonium salt, or organic amine salt thereof or a mono- or diester thereof with an alkyl of 1 to 4 carbon atoms, a monovalent sulfonic acid group or an alkali metal salt, alkaline earth metal salt, ammonium salt, or organic amine salt thereof or an ester thereof with an alkyl of 1 to 4 carbon atoms, or a monovalent sulfuric acid group or an alkali metal salt, alkaline earth metal salt, ammonium salt, or organic amine salt thereof or an ester thereof with an alkyl of 1 to 4 carbon atoms, providing that Y and Z, taken together, may be a group forming a ring through the medium of a divalent phosphoric acid group, divalent sulfonic acid group, or divalent sulfuric acid group.

The water-soluble copolymer mentioned above is obtained by a method for the manufacture of a water-soluble copolymer, which comprises copolymerizing 50 to 99.5 moles of at least one (meth)acrylic acid-based monomer represented by the formula III:

wherein, $R^1$ and X are as defined above, and 0.5 to 50 moles of at least one allyl ether-based monomer represented by the general formula IV:

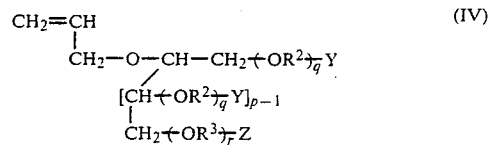

wherein, P, q, r. $R^2$, $R^3$, Y and Z are as defined above.

The novel water-soluble copolymer obtained by this invention is widely used such as for scale-preventing agents in cooling water systems and wet dust collecting systems, aqueous slurry dispersants for inorganic pigments, cement dispersants, and builders in detergents and exhibits outstanding properties in such applications.

PREFERRED EMBODIMENT OF THE INVENTION

Figure 1:
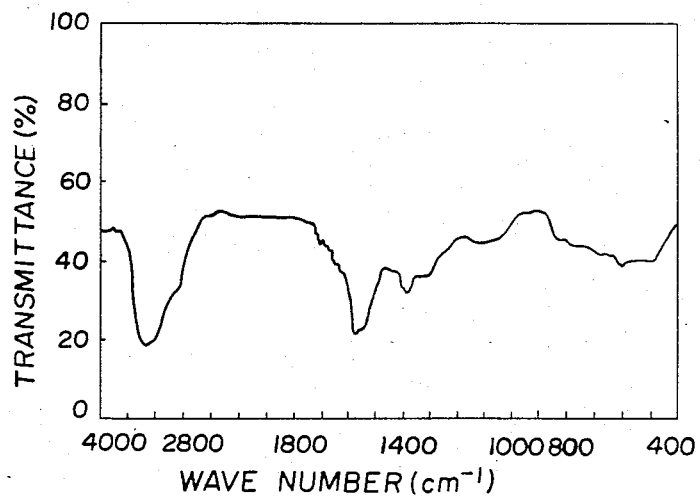
FIG. 1 is a diagram illustrating an infrared absorption spectrum of a water-soluble copolymer obtained in Example 1.

The water-soluble copolymer by the present invention comprises the repeating units represented respectively by the aforementioned general formulas I and II. In general formula I, $R^1$ denotes a hydrogen atom or methyl group, preferably a hydrogen atom, X denotes a hydrogen atom, alkali metal atom, alkaline earth metal atom, ammonium group or organic amine group, preferably an alkali metal atom or ammonium group, and most desirably an alkali metal atom. Examples of the alkali metal are sodium, potassium and lithium. Among the alkali metals, sodium or potassium proves to be particularly desirable. Examples of the alkaline earth metal are calcium and magnesium. Examples of the organic amine are aliphatic amines of 1 to 4 carbon atoms such as monomethylamine, dimethylamine, trimethylamine, monoethylamine, dieilylamine, triethylamine, isopropylamines and butylamines, alkanolamines such as monoethanolamine, diethanolamine, triethanolamine, monoisopropanolamine and diisopropanolamine, and pyridines. Among other organic amines, aliphatic amines and alkanolamines are particularly desirable.

In general formula II, p denoes an integer of the value of 1 to 4, preferably an integer of the value of 1 or 4, q and r independently denote 0 or an integer of the value of 1 to 100, preferably 0 or an integer of the value of 1 to 20, $R^2$ and $R^3$ independently denote an alkylene group of 2 to 4, preferably 2 to 3, carbon atoms, and Y and Z may be the same or different and denote a hydroxyl group, an alkoxy group of 1 to 4, preferably 1 to 2, carbon atoms, a monovalent phosphoric acid group or an alkali metal salt, alkaline earth metal salt, ammonium salt, or organic amine salt thereof or a mono- or di-ester thereof with an alkyl of 1 to 4, preferably 1 to 2, carbon atoms, a monovalent sulfonic acid group or an alkali metal salt, alkaline earth metal salt, ammonium salt, or organic amine salt thereof or an ester thereof with an alkyl of 1 to 4, preferably 1 to 2, carbon atoms, or a monovalent sulfuric acid group or an alkali metal salt, alkaline earth metal salt, ammonium salt, or organic amine salt thereof or an ester thereof with an alkali of 1 to 4, preferably 1 to 2, carbon atoms, providing that Y and Z, taken together, may form a ring through the medium of a divalent phosphoric acid group, divalent sulfonic acid group, or divalent sulfuric acid group. Preferably, Y and Z independently denote a hydroxyl group, an alkoxy group, a monovalent phosphoric acid group or the aforementioned salt or ester thereof, or a monovalent sulfonic acid group or the aforementioned salt or ester thereof. Most desirably, Y and Z independently denote a hydroxyl group, a monovalent phosphoric acid group, or a monovalent sulfonic acid group.

In the water-soluble copolymer of the present invention, the repeating units represented by general formula I account for 50 to 99.5 mol%, preferably 50 to 98 mol% and the repeating units represented by general formula II account for 50 to 0.5 mol%, preferably 50 to 2 mol%. The number-averaged molecular weight of the copolymer is 300 to 100,000, preferably 500 to 20,000.

The water-soluble copolymer mentioned above is obtained by the copolymerization of 50 to 99.5 moles, preferably 50 to 98 moles, of at least one (meth)acrylic acid-based monomer represented by the general formula III:

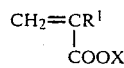

wherein, $R^1$ and X are as defined above, and 0.5 to 50 moles, preferably 2 to 50 moles, of at least one allyl ether-based monomer represented by the general formula IV:

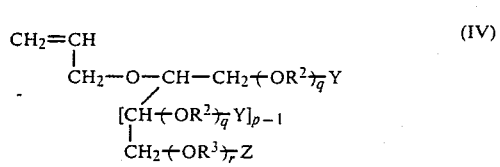

wherein, p, q, r, $R^2$, $R^3$, Y and Z are as defined above.

Examples of the (meth)acrylic acid-based monomer of general formula III to be used in the present invention are acrylic acid, sodium acrylate, potassium acrylate, lithium acrylate, ammonium acrylate, methacrylic acid, sodium methacrylate, potassium methacrylate, lithium methacrylate and ammonium methacrylate.

Examples of the allyl ether-based monomer of general formula IV are 3-allyloxypropane-1,2-diol, 2-allyloxypropane-2-ol-1-phosphate, 3-allyloxypropane-2-ol-1-sulfate, 3-allyloxy-1,2-di(poly)oxyethylene ether propane, 3-allyloxy-2-(poly)oxyethylene-1-phospha-(poly)oxyethylene ether propane, 3-allyloxy-2-(poly)oxyethylene-1-sulfo-(poly)oxyethylene ether propane, 3-allyloxy-1,2-di(poly)oxypropylene ether propane, 3-allyloxy-2-(poly)oxypropylene-1-phospho-(poly)oxypropylene ether propane, 3-allyloxy-2-(poly)oxypropylene-1-sulfo-(poly)oxypropylene ether propane, 6-allyloxy hexane-1,2,3,4,5-pentaol, 6-allyloxy hexane-2,3,4,5-tetraol-1-phosphate, 6-allyloxy hexane-2,3,4,5-tetraol-1-sulfonate, 6-allyloxy-1,2,3,4,5-penta(poly)oxyethylene ether hexane, 6-allyloxy-1,2,3,4,5-penta(poly)oxypropylene ether hexane, 3-allyloxy-2-hydroxypropane-1-sulfonic acid and alkali metal salts, alkaline earth metal salts, ammonium salt, and organic amine salts thereof, phosphoric esters and sulfuic esters of such compounds, and alkali metal salts, alkaline earth metal salts, ammonium salts, and organic amine salts of such esters; 3-allyloxy-2-(poly)oxyethylene-1-sulfo-(poly)oxyethylene ether propane and alkali metal salts, alkaline earth metal salts, ammonium salt, and organic amine salts thereof, phosphoric esters and sulfuric esters of such compounds, and alkali metal salts, alkaline earth metal salts, ammonium salts, and organic amine salts of such esters; and 3-allyloxy-2-(poly)oxypropylene propane sulfonic acid and alkali metal salts, alkaline earth metal salts, ammonium salt, and organic amine salts thereof, phosphoric esters and sulfuric esters of such compounds, and alkali metal salts, alkaline earth metal salts, ammonium salts, and organic amine salts of such esters.

Among all these allyl ether-based monomers of the general formula IV, those of the general formula wherein p is an integer of the value of 1 or 4 are advantageous in respect that they are readily available commercially.

For the production of the novel water-soluble copolymer from the (meth)acrylic acid-based monomer (III) and the allyl ether-based monomer (IV), any of the conventional methods available for the copolymerization of the type involved herein may be effectively adopted. For example, a method of polymerization which is effected in water, in an organic solvent, or a mixed solvent consisting of a water-soluble organic solvent and water may be adopted. When the polymerization is carried out in an aqueous medium, a persulfate of ammonium or alkali metal or a peroxide such as hydrogen peroxide or t-butyl hydroperoxide is used as a polymerization initiator and an accelerator such as sodium hydrogen sulfite or ascorbic acid may be additionally used. When the polymerization is carried out in an organic solvent, an azo type compound such as azobisisobutylonitrile or an organic peroxide such as benzoyl peroxide, lauroyl peroxide, or other peroxide, cumene hydroperoxide or other hydroperoxide is used as a polymerization initiator and an accelerator such as an amine compound may be additionally used. When the polymerization is carried out in a mixed solvent consisting of a water-soluble organic solvent and water, a polymerization initiator selected suitably from among the various polymerization initiators enumerated above is used alone or optionally in combination with one accelerator similarly selected from among the various accelerators mentioned above.

The polymerization initiator is used in an amount of 0.05 to 20% by weight, preferably 0.1 to 10% by weight, based on the total amount of the monomers.

The polymerization temperature is suitably fixed depending on the particular types of solvent and polymerization initiator to be used. Generally it falls in the range of 50° to 200° C., preferably 80° to 150° C. The reaction time is in the range of 20 to 500 minutes, preferably 30 to 400 minutes.

The novel water-soluble copolymer obtained as described above can be used in its unaltered form in various applications. Optionally, it may be further neutralized with an alkaline substance before it is put to use. Examples of the alkaline substance usable for the neutralization are hydroxides, chlorides, and carbonates of alkali metals and alkaline earth metals; ammonia; and organic amines.

The water-soluble copolymer of the present invention is widely used such as for scale-preventing agents (scale inhibitors) in cooling water systems and wet dust collecting systems, aqueous slurry dispersants in inorganic pigments, cement dispersants, and builders in detergents, for example, and manifest outstanding properties in these applications.

The ratio of the component unit represented by the aforementioned general formula (I) to the component unit represented by the aforementioned general formula (II) in the molecule of the water-soluble copolymer mentioned above is desired to be 50 to 99.5 mol% of the former to 50 to 0.5 mol% of the latter (providing that the sum of the two component units is 100 mol%). When the ratio of the component unit (I) to the component unit (II) falls within the range mentioned above, the water-soluble copolymer used in such applications as enumerated above is allowed to manifest its outstanding properties to better advantage owing to the dispersing effect of each of of the component unit (I) and the component unit (II). For the production of the water-soluble copolymer from a (meth)acrylic acid-based monomer (III) and an allyl ether-based monomer (IV), the charging ratio of these two monomers is desired to be selected so that the ratio of the component unit (I) to the component unit (II) in the molecule of the produced copolymer will fall in the range of 50 to 99.5 mol% of the former to 50 to 0.5 mol% of the latter (providing that the sum of the two component units is 100 mol%).

Now, the present invention will be described more specifically below with reference to working examples. Needless to mention, the present invention is not limited only to these examples. Wherever percents are mentioned, they are meant % by weight unless otherwise specified.

EXAMPLE 1

In a four-necked flask provided with a reflux condenser and having an inner volume of 1 liter, 165 g of purified water was placed and kept stirred at 90° C. and 620 1 g of an aqueous 30% sodium acrylate solution, 15 g of 3-allyloxy-1,2-dihydroxy propane, and 200 g of an aqueous 3% ammonium persulfate solution were independently added dropwise to the stirred water over a period of 3.5 hours to induce polymerization of the monomers and afford a light yellow, transparent reaction solution. When the reaction solution was assayed for its unaltered monomer content by the bromination method (similarly adopted in the following working examples), the results indicated the conversion to be 95%. As determined by the gel permeation chromatography (similarly adopted in the following working examples), the number-averaged molecular weight of the water-soluble copolymer (I) was found to be 4,400. After the water-soluble copolymer (1) was purified by precipitation in methanol and dried, it gave an infrared absorption spectrum wherein absorptions due to —O—, —CO— and —OH were clearly observed. When the dried water-soluble copolymer (1) was dissolved in D$_2$O and subjected to NMR analysis, it showed absorptions of

The infrared absorption spectrum of the water-soluble copolymer (1) is shown in FIG. 1.

EXAMPLE 2

In the same polymerization reactor as used in Example 1, the polymerization by the procedure of Example 1 was carried out, except that 91 g of purified water, 437 g of an aqueous 30% potassium methacrylate, 72 g of an aqueous 40% solution of 3-allyloxy-1,2-dihydroxypropane monophosphate obtained by the reaction of 1 mole of 3-allyloxy-1,2-dihydroxypropane with 0,5 mole of phosphorus pentoxide, and 200 g of an aqueous 3% ammonium persulfate solution were used instead. The reaction produced a yellow, transparent aqueous solution of a water-soluble copolymer (2). The conversion was 95% and the number-averaged molecular weight of the water-soluble copolymer (2) was 3,600.

EXAMPLE 3

Figure 2:
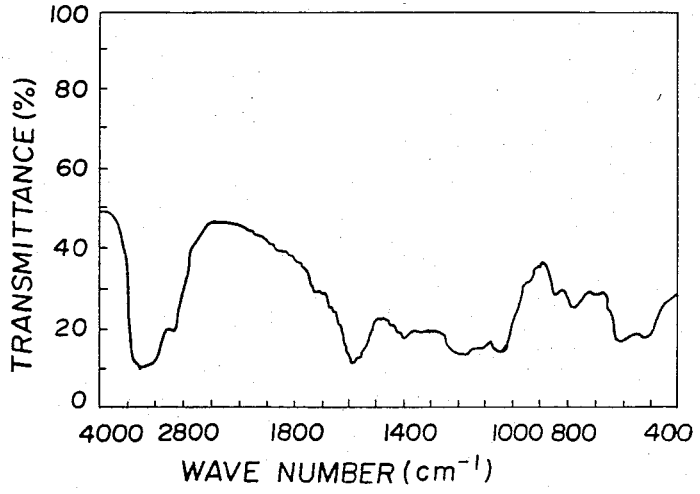
FIG. 2 is a diagram illustrating an infrared absorption spectrum of a water-soluble copolymer obtained in Example 3.

In the same polymerization reactor as used in Example 1, the polymerization by the procedure of Example 1 was carried out, except that 249 g of purified water, 406 g of an aqueous 35% sodium acrylate solution, and 145 g of an aqueous 40% sodium 3-allyloxy-2-hydroxypropane sulfonate were used instead. The reaction produced a red, transparent aqueous solution of a water-soluble copolymer (3). The conversion was 94% and the number-averaged molecular weight of the water-soluble copolymer (3) was 4,900. The infrared absorption spectrum of this copolymer is shown in FIG. 2.

EXAMPLE 4

In the same polymerization reactor as used in Example 1, the polymerization by the procedure of Example 1 was carried out, except that 370 g of purified water was placed in the reactor, then 100 g of an allyl ether-based monomer obtained by the addition of 10 moles of ethylene oxide to 3-allyloxy-1,2-dihydroxypropane in the presence of powdered sodium hydroxide as a catalyst was dissolved in the purified water, and subsequently 330 g of an aqueous 30% potassium methacrylate solution was added dropwise over a period of 3.5 hours. The polymerization produced a reddish brown, transparent aqueous solution of a water-soluble copolymer (4). The conversion was 90% and the number-averaged molecular weight of the water-soluble copolymer (4) was 6,500.

EXAMPLE 5

In the same polymerization reactor as used in Example 1, the polymerization by the procedure of Example 1 was carried out, except that 248 g of purified water, 422 g of an aqueous 35% sodium acrylate, and 130 g of an aqueous 40% solution of an allyl ether-based monomer obtained by adding 2 moles of propylene oxide to 3-allyloxy-1,2-dihydroxypropane and subsequently causing 0.5 mole of phosphorus pentoxide to react upon the addition product were used instead. The polymerization produced a yellow, transparent solution of a water-soluble copolymer (5). The conversion was 95% and the number-averaged molecular weight of the water-soluble copolymer (5) was 4,500.

EXAMPLE 6

In the same polymerization reactor as used in Example 1, the polymerization by the procedure of Example 1 was carried out, except that 240 g of purified water, 520 g of an aqueous 35% sodium acrylate, and 40 g of an aqueous 50% monoallyl sorbitol ether solution were used instead. This polymerization produced a yellow, transparent aqueous solution of a water-soluble copolymer (6). The conversion was 97% and the number-averaged molecular weight of the water-soluble copolymer (6) was 4,400.

EXAMPLE 7

In the same polymerization reaction as used in Example 1, the polymerization by the procedure of Example 1 was carried out, except that 250 g of purified water, 410 g of an aqueous 35% sodium acrylate, and 140 g of an aqueous 40% solution of 3-allyloxy-1,2-dihydroxypropane monosulfate obtained by the reaction of 1 mole of 3-allyloxy-1,2-dihydroxypropane with 0.5 mole of sulfuric acid. The reaction produced a aqueous solution of a water-soluble copolymer (7). The conversion was 94% and the number-averaged molecular weight of the water-soluble copolymer (7) was 5,000.

EXAMPLE 8

By the procedure described below, a varying water-soluble copolymer was tested for its effect in curbing formation of scale in a water system. In glass jars having an inner volume of 225 mol, 170 g of water and 10 g of an aqueous 1.56% calcium chloride dihydrate solution were each placed as mixed with varying amounts, 1 g, 5 g and 10 g, of aqueous 0.02% solutions of the water-soluble copolymers (1), (2), (3), (6) and (7) obtained in Example 1, 2, 3, 6 and 7 (corresponding respectively to 1 ppm, 5 ppm and 10 ppm based on the supersaturated aqueous solutions produced consequently). By further addition of 10 g of an aqueous 3% sodium bicarbonate solution, a supersaturated aqueous solution of 530 ppm of calcium carbonate was obtained. Then, the glass jars were tightly stoppered and subjected to a thermal treatment at 70° C. for three hours. They were then cooled and the precipitates formed in the jars were separated by use of a membrane filter 0.45 μm in mesh size. The resultant filtrates were assayed by Japanese Industrial Standard (JIS) K-0101. The results are shown in Table 1.

For the purpose of comparison, the procedure described above was repeated by omitting the use of water-soluble copolymers in some test runs and by using sodium polyacrylate of a number-averaged molecular weight of 4,000 in the place of water-soluble copolymers in other test runs. The results are shown in Table 1.

TABLE 1
Effect in curving of scale in cooling water model

| | Amount added (ppm) | Test pH | Suspension of matter in test solution | $CaCO_3$ content of filtrate (ppm) | (Note 1) Ratio of curbing (%) |
|---|---|---|---|---|---|
| Water-soluble copolymer (1) | 1 | 8.0 | no suspension | 480 | 85 |
| | 5 | 8.1 | no suspension | 505 | 93 |
| | 10 | 8.1 | no suspension | 530 | 100 |
| Water-soluble copolymer (2) | 1 | 8.0 | no suspension | 495 | 90 |
| | 5 | 8.1 | no suspension | 520 | 97 |
| | 10 | 8.1 | no suspension | 530 | 100 |
| Water-soluble copolymer (3) | 1 | 7.9 | no suspension | 510 | 94 |
| | 5 | 8.0 | no suspension | 530 | 100 |
| | 10 | 8.1 | no suspension | 535 | 100 |
| Water-soluble copolymer (6) | 1 | 8.0 | no suspension | 490 | 88 |
| | 5 | 8.1 | no suspension | 510 | 94 |
| | 10 | 8.1 | no suspension | 530 | 100 |
| Water-soluble copolymer (7) | 1 | 7.9 | no suspension | 500 | 91 |
| | 5 | 8.0 | no suspension | 520 | 97 |
| | 10 | 8.1 | no suspension | 530 | 100 |
| No copolymer added | — | 7.0 | no suspension | 190 | 0 |
| Sodium polyacrylate | 1 | 7.4 | suspension | 250 | 18 |
| | 5 | 7.6 | suspension | 470 | 82 |
| | 10 | 7.6 | no suspension | 520 | 97 |

(Note 1)

Curbing ratio $= \frac{C - B}{A - B} \times 100$

A: $CaCO_3$ concentration (=530) before thermal treatment
B: $CaCO_3$ concentration (=190) in filtrate after test in the absence of a scale-preventing agent
C: $CaCO_3$ concentration in filtrate after test As shown in Table 1, the novel water-soluble copolymers according to the present invention have an outstanding ability to prevent formation of scale in cooling water.

EXAMPLE 9

Figure 3:
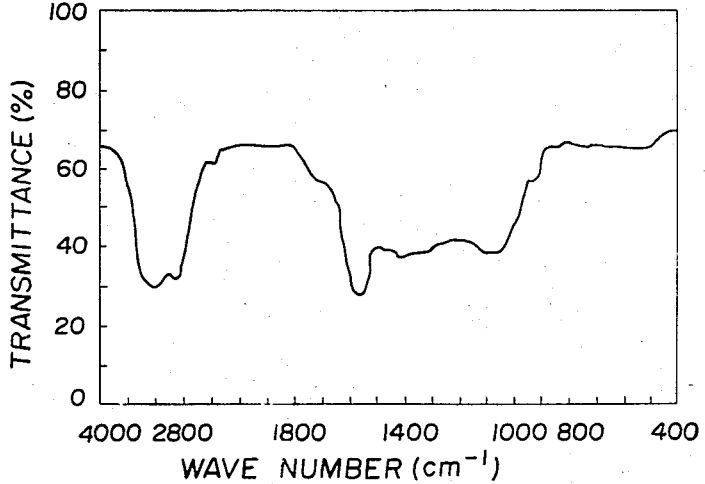
FIG. 3 is a diagram illustrating an infrared absorption spectrum of a water-soluble copolymer obtained in Example 8.

In the same polymerization reactor as used in Example 1, the polymerization by the procedure of Example 1 was carried out, except that 142 g of purified water, 600 g of an aqueous 30% sodium acrylate solution, 38 g of an aqueous 60% sodium 3-allyloxy-2-hydroxypropane sulfonate solution, and 200 g of an aqueous 3% ammonium persulfate solution were used instead. The reaction produced an aqueous solution of a water-soluble copolymer (8). The conversion was 96% and the number-averaged molecular weight of the water-soluble copolymer (8) was 4,400. After the water-soluble copolymer (8) was purified by precipitation in methanol and then dried, it gave an infrared absorption spectrum in which absorptions due to —O—, —CO— and —OH were clearly observed. (The infrared absorption spectrum of the copolymer is shown in FIG. 3) When the dry water-soluble copolymer (8) was dissolved in $D_2O$ and subjected to NMR analysis, absorptions of

were clearly observed.

EXAMPLE 10

In the same polymerization reactor as used in Example 1, 150 g of purified water was place and 140 g of an allyl ether-based monomer obtained by adding 5 moles of ethylene oxide to sodium 2-allyloxy-2-hydroxypropane sulfonate in the presence of sodium hydroxide as a catalyst was dissolved in the water. Subsequently, the resultant solution was kept stirred at 100° C., 170 g of an aqueous 35% potassium methacrylate solution, 150 g of an aqueous 6% ammonium persulfate solution, and 50 g of an aqueous 6% hydrogen peroxide were independently added dropwise to the stirred solution over a period of 3.5 hours to induce polymerization of the monomers and afford an aqueous solution of a water-soluble copolymer (9). The conversion was 90% and the number-averaged molecular weight of the water-soluble copolymer (9) was 1,600.

EXAMPLE 11

In the same polymerization reactor as used in Example 1, 132 g of purified water was placed and 95 g of an allyl ether-based monomer obtained by adding 2 moles of propylene oxide to sodium 3-allyloxy-2-hydroxypropane sulfonate in the presence of sodium hydroxide as a catalyst and subsequently causing 0.5 mole of phosphorus pentoxide to react upon the resultant addition product was added. The water and the monomer were kept stirred at 100° C. and 300 g of an aqueous 35% potassium acrylate solution, 150 g of an aqueous 6% ammonium persulfate solution, and 50 g of an aqueous 6% hydrogen peroxide solution were independently added dropwise to the stirred solution, to afford an aqueous solution of a water-soluble copolymer (10). The conversion was 94% and the number-averaged molecular weight of the water-soluble copolymer (10) was 2,200.

EXAMPLES 12-14

By following the procedure described below, a varying water-soluble copolymer was tested for its ability to disperse inorganic pigments. Stainless steel beakers having an inner volume of 1000 ml were charged with 400 g of 25% paste of satin white (calcium sulfoaluminate hexahydrate) and the water-soluble copolymer (8) through (10) obtained in Example 9-11 were severally added in a fixed amount of 2.0 g as solids (solid-solid 2.0%). The contents of the beakers were stirred at 2000 rpm for 15 minutes with a disperser provided with dissolver type blades. The stirred contents were tested for viscosity at 25° C. The results are shown in Table 2.

COMPARATIVE EXPERIMENT 1

A dispersion of satin white was prepared by following the procedure of Example 12, except that 5.0 g of an aqueous 40% sodium polyacrylate having a number-averaged molecular weight of 5,000 and available in the market was used. This dispersion was tested for viscosity. The results are shown in Table 2.

TABLE 2

| | | | Ability of disperse satin white | |
|---|---|---|---|---|
| | | | Viscosity of dispersion (cps) at 25° C. | |
| | Dispersant | Amount added (solid/solid, %) | Immediately after dispersion | On elapse of 24 hours from dispersion |
| Example 12 | Water-soluble copolymer (8) | 2.0 | 10 | 10 |
| Example 13 | Water-soluble copolymer (9) | 2.0 | 12 | 12 |
| Example 14 | Water-soluble copolymer (10) | 2.0 | 7 | 7 |
| Comparative Experiment 1 | Sodium polyacrylate | 2.0 | 80 | 80 |

As shown in Table 2, the novel water-soluble copolymers according to the present invention possess an outstanding ability to disperse pigments.

EXAMPLE 15

In the same polymerization reactor as used in Example 1, 130 g of purified water was placed and 90 g of 3-allyloxy-1,2-dihydroxy propane was dissolved in the water. The resultant solution was heated to 90° C. and kept stirred at this temperature, and 430 g of an aqueous 35% sodium acrylate solution, 150 g of an aqueous 6% ammonium persulfate solution, and 50 g of an aqueous 6% hydrogen peroxide solution were independently added dropwise to the stirred solution over a period of 3.5 hours to induce copolymerization of the monomers and afford an aqueous solution of a water-soluble copolymer (11). The number-averaged molecular weight of this water-soluble copolymer (11) was 4,400.

EXAMPLE 16

In the same polymerization reactor as used in Example 1, 140 g of purified water was placed and 60 g of sodium 2-allyloxy-2-hydroxypropane sulfonate was dissolved in the water. The resultant solution was heated to 90° C. and kept stirred at this temperature, and 400 g of an aqueous 35% ammonium acrylate solution and 200 g of an aqueous 5% ammonium persulfate solution were independently added dropwise to the stirred solution over a period of 3.5 hours to induce copolymerization of the monomers and afford and aqueous solution of a water-soluble copolymer (12). The number-averaged molecular weight of this water-soluble copolymer (12) was 4,600.

EXAMPLE 17

In a stainless steel beaker having an inner volume of 1 liter, 65 g of water was placed, 1.3 g of an aqueous solution of the water-soluble copolymer (11) (solid-solid 0.2%) was added thereto, and they were stirred with a disperser. To the stirred solution, 200 g of finely powdered calcium carbonate (having an average particle diameter of 1.5μ) was added. After completion of the addition, the stirring was continued at 2000 rpm for 15 minutes. The resultant 75% dispersion was tested for viscosity at 25° C. The results are shown in Table 3.

EXAMPLE 18

By following the procedure of Example 17, a 75% dispersion of calcium carbonate incorporating 0.2% as solids of the water-soluble copolymer (12) was prepared. The dispersion was tested for viscosity. The results are shown in Table 3.

COMPARATIVE EXPERIMENT 2

The procedure of Example 17 was repeated, except that commercially available sodium polyacrylate having a molecular weight of 5,000 was used in the place of the water-soluble copolymer (11). The resultant dispersion was tested for viscosity. The results are shown in Table 3.

TABLE 3

| | | Viscosity of dispersion incorporating 0.2% of dispersant (cps) | |
|---|---|---|---|
| | Dispersant for inorganic pigment | Immediately after dispersion | On elapse of 24 hours from dispersion |
| Example 17 | Copolymer (11) | 92 | 92 |
| Example 18 | Copolymer (12) | 78 | 78 |
| Comparative Experiment 2 | Sodium polyacrylate | 80 | 80 |

As shown in Table 3, the dispersion of inorganic pigments using water-soluble copolymers of the present invention possess outstanding ability to disperse pigments. What is claimed is:

1. A water-soluble copolymer, comprising 50 to 99.5 mol% of repeating units represented by the general formula I:

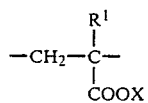

wherein, $R^1$ denotes A hydrogen atom or methyl group and X a hydrogen atom, alkali metal atom, alkaline earth metal atom, ammonium group or organic amine group, and 50 to 0.5 mol% of repeating units represented by the general formula II:

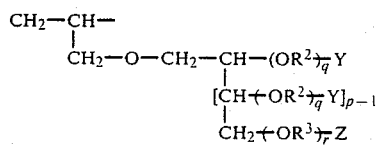

wherein, p denotes an integer of the value of 1 to 4, q and r independently denote O or an integer of the value of 1 to 100, $R^2$ and $R^3$ independently denote an alkylene group of 2 to 4 carbon atoms, Y denotes a hydroxyl group, and Z denotes a monovalent sulfonic acid group or an alkali metal salt thereof.

2. A copolymer according to claim 1, wherein q and r independently denote 0 or an integer having the value of 1 to 20.

3. A copolymer according to claim 1, wherein X denotes an alkali metal atom or ammonium group.

4. A copolymer according to claim 1, wherein X denotes an alkali metal atom.

5. A copolymer according to claim 1, wherein $R^1$ denotes a hydrogen atom.

6. A copolymer according to claim 1, wherein $R^1$ denotes a hydrogen atom and X an alkali metal atom.

7. A copolymer according to claim 1, wherein p denotes 1 or 4.

8. A copolymer according to claim 7, wherein q and r independently denote 0.

9. A copolymer according to claim 1, wherein the repeating units represented by the general formula I account for 50 to 98 mol% and the repeating units represented by the general formula II for 50 to 2 mol%.

10. A method for the manufacture of a water-soluble copolymer comprising 50 to 99.5 mol% of repeating units represented by the general formula I:

wherein, $R^1$ and X are as defined above, and 50 to 0.5 mol% of repeating units represented by the general formula II:

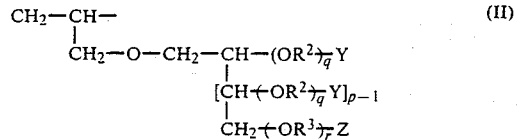

wherein, p, q, r, $R^2$, $R^3$, Y and Z are as defined above, which method comprises copolymerizing 50 to 99.5 moles of at least one acrylic acid-based monomer represented by the formula III:

wherein, $R^1$ and X are as defined above, and 0.5 to 50 moles of at least one allyl ether-based monomer represented by the general formula IV:

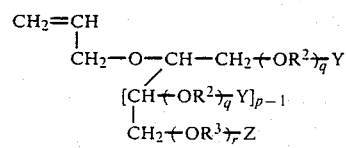

wherein, p, q, r, $R^2$, $R^3$, Y and Z are as defined above.

11. A method according to claim 10, wherein the reaction is carried out in the presence of 0.05 to 20% by weight, based on the total amount of the monomers, of a polymerization initiator at a temperature in the range of 50° to 200° C.

12. A method according to claim 11, wherein the reaction is carried out at a temperature in the range of 80° to 150° C.

13. A method according to claim 10, wherein q and r independently denote 0 or an integer having the value of 1 to 20.

14. A method according to claim 10, wherein X denotes an alkali metal atom or ammonium group.

15. A method according to claim 10, wherein X denotes an alkali metal atom.

16. A method according to claim 10, wherein $R^1$ denotes a hydrogen atom.

17. A method according to claim 15, wherein $R^1$ denotes a hydrogen atom and X an alkali metal atom.

18. A method according to claim 15, wherein p denotes 1 or 4.

19. A method according to claim 18, wherein q and r independently denote 0.

20. A method according to claim 15, wherein the repeating units represented by the general formula I account for 50 to 98 mol% and the repeating units represented by the general formula II or 50 to 2 mol%.

21. A scale inhibitor having as main component thereof the water-soluble copolymer set forth in claim 1.

22. A pigment dispersant having as main component thereof the water-soluble copolymer set forth in claim 1.

* * * * *